(12) United States Patent
Bilanovic et al.

(10) Patent No.: US 7,727,747 B2
(45) Date of Patent: Jun. 1, 2010

(54) SOLID OR SEMI-SOLID STATE FERMENTATION OF XANTHAN ON POTATO OR POTATO WASTE

(75) Inventors: Dragoljub D. Bilanovic, Bemidji, MN (US); Samuel Hunter Malloy, Bemidji, MN (US); Petra Remeta, Bemidji, MN (US)

(73) Assignee: Bemidji State University Foundation, Bemidji, MN (US)

( * ) Notice: Subject to any disclaimer, the term of this patent is extended or adjusted under 35 U.S.C. 154(b) by 831 days.

(21) Appl. No.: 11/598,907

(22) Filed: Nov. 14, 2006

(65) Prior Publication Data

US 2008/0113414 A1 May 15, 2008

(51) Int. Cl.
C12P 19/06 (2006.01)
C12P 19/04 (2006.01)

(52) U.S. Cl. .......................... 435/104; 435/101

(58) Field of Classification Search ........................ None
See application file for complete search history.

(56) References Cited

U.S. PATENT DOCUMENTS

| | | | |
|---|---|---|---|
| 4,245,046 A | 1/1981 | Demain et al. | |
| 4,282,321 A | 8/1981 | Wernau | |
| 4,328,308 A | 5/1982 | Weisrock | |
| 4,328,310 A | 5/1982 | Weisrock | |
| 4,352,882 A | 10/1982 | Maury | |
| 4,940,663 A | 7/1990 | Eyssautier | |
| 5,434,078 A | 7/1995 | Pollock et al. | |
| 5,480,785 A | 1/1996 | Troostembergh et al. | |
| 5,580,763 A | 12/1996 | Honma et al. | |
| 5,864,034 A | 1/1999 | Murofushi et al. | |
| 5,972,695 A | 10/1999 | Murofushi et al. | |
| 6,110,731 A | 8/2000 | Murofushi et al. | |
| 6,251,446 B1 * | 6/2001 | Hoppe et al. | 426/48 |

FOREIGN PATENT DOCUMENTS

| EP | 0 032 293 A2 | 7/1981 |
|---|---|---|
| EP | 0 066 957 A1 | 12/1982 |
| WO | WO 00/78967 A1 | 12/2000 |

OTHER PUBLICATIONS

Stredansky M., et al., "Xanthan production by solid state fermentation," from *Process Biochemistry 34*, pp. 581-587, (1999).

Seong, D., et al., "Xanthan gum production from waste sugar beet pulp," from *Process Biochemistry 70*, pp. 105-109, (1999).

Papagianni, M., et al., "Xanthan production by *Xanthomonas campestris* in batch cultures," from *Process Biochemistry 37*, pp. 73-80 (2001).

Lopez, M. J., et al., "*Xanthomonas Campestris* Strain Selection for Xanthan Production from Olive Mill Wastewaters," from *Wat. Res.*, vol. 35, No. 7, pp. 1828-1830 (2001).

Bilanovic, D., et al., "Xanthan Fermentation of Citrus Waste," from *Bioresource Technology 48*, pp. 169-172 (1994).

Souw, P., et al., "Nutritional Studies on Xanthan Production by *Xanthomonas campestris* NRRL B1459," from *Applied and Environmental Microbiology*, pp. 1186-1192 (1979).

Nitschke, M., et al., "Formulacao De Memos De Cultivo a Base De Soro De Leite Para a Producao De Goma Xantana Por X. *Campestris* $C_7L^1$," Summary, from *Cienc. Tecnol. Aliment., Campinas, 21(1)*, pp. 82-85 (2001).

Jansson, P., et al., "Structure of the extracellular polysaccharide from *Xanthomonas campestris*," abstract from *Carbohydrate Research*, vol. 45, Issue 1, pp. 275-282 (1975).

Giannouli, P., "Cryogelation of xanthan," from *Food Hydrocolloids 17*, pp. 495-501 (2003).

Corneliu, I., et al., "Superabsorbant hydrogels based on xanthan and poly(vinyl alcohol)—1. The study of the swelling properties," from *Euro. Poly. J.* 38 (2002) ; 2313-2320.

Letisse, F., et al., "The influence of metabolic network structures and energy requirements on xanthan gum yields," from *Journal of Biotechnology 99*, pp. 307-317 (2002).

Cacik, F., et al., "Optimal control of a batch bioreactor for the production of xanthan gum," from *Computers and Chemical Engineering 25*, pp. 409-418 (2001).

Lo, Y., et al., "Kinetic and feasibility studies of ultrafiltration of viscous xanthan gum fermentation broth," from *Journal of Membrane Science 117*, pp. 237-249 (1996).

Rosalam, S., et al., "Review of xanthan gum production from unmodified starches by *Xanthomonas comprestris* sp.," from *Enzyme and Microbial Technology 39*, pp. 197-207 (2006).

Serrano-Carreon, L., et al., "Prediction of xanthan fermentation development by a model linking kinetics, power drawn and mixing," from *Process Biochemistry*, vol. 33, No. 2, pp. 133-146 (1998).

* cited by examiner

*Primary Examiner*—Maury Audet
(74) *Attorney, Agent, or Firm*—Kinney & Lange, P.A.

(57) ABSTRACT

The present invention presents a method for the aerobic production of xanthan by bacteria of the genus *Xanthomonas* on a solid or semi-solid substrate. In the exemplary embodiment of the method, a substrate is provided that has a total solids content of about 6.5% or higher. The substrate is sterilized and cooled. Bacteria of the genus *Xanthomonas* are inoculated into the substrate and incubated. After incubation, the bacteria are destroyed, the substrate is either diluted or washed, and the xanthan is isolated.

19 Claims, 1 Drawing Sheet

SOLID OR SEMI-SOLID STATE FERMENTATION OF XANTHAN ON POTATO OR POTATO WASTE

CROSS-REFERENCE TO RELATED APPLICATION(S)

None.

BACKGROUND OF THE INVENTION

The invention relates to a fermentation process for producing xanthan gum using bacteria of the genus *Xanthomonas*.

Xanthan, or xanthan gum, is excreted by bacteria of the genus *Xanthomonas*, for example *Xanthomonas campestris* NRRL B-1003, NRRL B-1459, NRRL B-1043, or related organisms. The length of a xanthan molecule varies as a function of the: i) bacterium strain used, ii) composition of culture media, and iii) downstream processing; its average molecular weight is reported in the range of $2\times10^6$ to $5\times10^7$ Daltons (Da). The xanthan primary chain is made of β-d-glucose monomers; the side chains are linked to the primary chain at every second glucose and are composed of one glucuronic acid sited in-between two D-mannose.

Industrial production of xanthan started in the mid 1970s and today the hetero-polysaccharide is widely used as an emulsifier, stabilizer, thickener, and friction and water mobility reducer in industries as different as food and petroleum. Numerous xanthan based products have been developed, for example: i) xanthan-cryogels, which could replace gelatin in the food industry thereby eliminating potential BSE related problems while meeting the needs of vegetarians and populations not consuming cattle or pigs, and ii) xanthan-hydrogels, which could be used in pH and similar sensors. With an estimated worldwide production of over 40,000 tons per year and a price of about $7-8 per kilogram (as reported in 2002), xanthan is the most important, industrially produced, microbial hetero-polysaccharide.

In industry, xanthan is usually produced by aerobic submerged fermentation conducted in a batch-mode for up to five days. To minimize oxygen transfer and viscosity problems in the submerged fermentation, the broth is either made of a very large amount of water and a relatively low concentration of nutrients or a very large amount of water and a sequential addition of nutrients, which results in a lower concentration of nutrients. The fermentation process requires a carbon source, which is commonly glucose, sucrose, or starch in concentrations of 1-5%. The concentration and the type of carbon source and the carbon-to-nitrogen ratio of the substrate are important because these factors affect the xanthan yield. After fermentation, xanthan is precipitated from the pasteurized fermentation broth with ethanol, methanol, isopropyl or similar alcohols. Not less than two, but often more than three volumes of alcohol per volume of broth may be required for precipitation. Therefore, large amounts of solvents are needed to extract xanthan from the fermentation broth because of the high water content of the broth. Following extraction, the raw xanthan is dried, milled, and packed for further use or purification.

Alternative carbon sources have been tested on xanthan fermentation, for example: apple pomace, spent malt grains, citrus waste, olive-mill wastewater, sugar beet pulp, and whey. Solubilized residues of cassava, cassava bagasse, potatoes, husks and pulp of coffee beans have also been tested on xanthan fermentation. With the exception of the citrus waste, apple pomace, and spent malt grains works, all other works on xanthan fermentation using residues from the agro- or food industry were conducted following the release of simple sugars from the residues by means of an enzymatic, acid, or base treatment. Additionally, a number of improvements concerning aerobic submerged fermentation of xanthan have been developed to increase xanthan yield.

Xanthan fermentation is characterized by a significant increase in the viscosity of the fermentation medium, which limits the transfer of oxygen and other chemicals to the *Xanthomonas campestris* bacteria while decreasing both the xanthan yield and quality. It is highly desirable to maintain the appropriate supply of oxygen and other chemicals to the bacteria while minimizing the energy requirements pertinent to oxygen supply and mixing caused by utilization of power intensive aerating and mixing devices. It is also highly desirable to increase the xanthan production while decreasing, preferably eliminating in full, the large volumes of water involved in aerobic submerged xanthan fermentation. Such fermentation would have a higher yield of xanthan, require much less solvents for extracting the xanthan from the broth, and, consequently, yield substantial economical, environmental, and technological benefits for xanthan producing plants and is the subject of this invention.

BRIEF SUMMARY OF THE INVENTION

The present invention presents a method for the aerobic production of xanthan by bacteria of the genus *Xanthomonas* on a solid or semi-solid substrate that comprises a complex starch medium. In one embodiment of the method, a substrate is provided that has a total solids content of about 6.5% or higher. The substrate is sterilized and cooled. Bacteria of the genus *Xanthomonas* is inoculated into the substrate and incubated. Substrate is sterilized after incubation then it is either diluted or washed with water. Xanthan is then isolated from either diluted substrate or from the wash-water.

DETAILED DESCRIPTION

Figure 1:
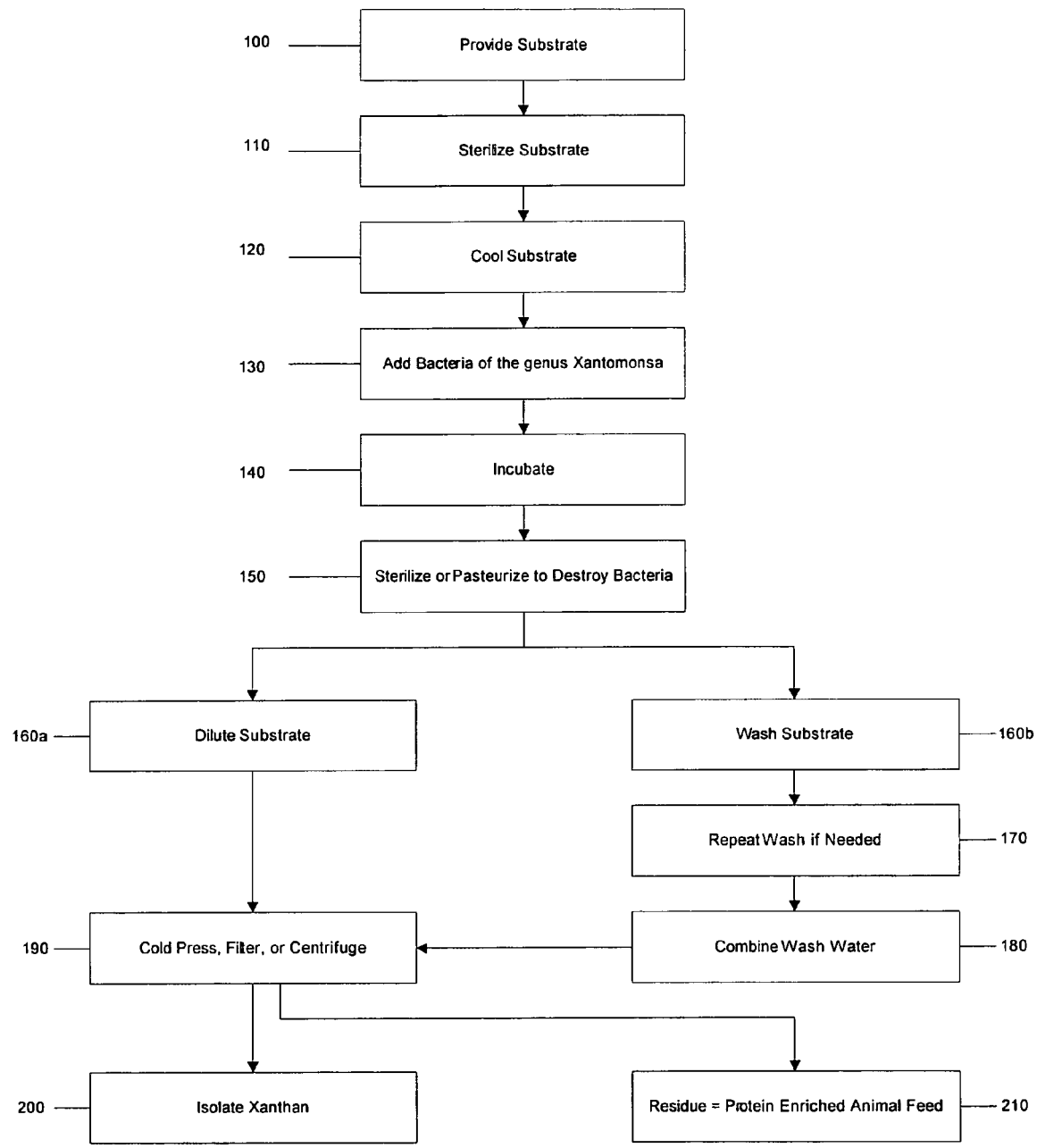
FIG. 1 is a block diagram showing an exemplary embodiment of the claimed method.

FIG. 1 shows a fermentation method for the aerobic production of xanthan by bacteria of the genus *Xanthomonas* on a solid or semi-solid substrate. Step 100 in FIG. 1 represents providing a substrate. In the exemplary embodiment, provision of the substrate comprises providing a complex starch medium, providing a fermentation vehicle, adding nutrients to the substrate and, if needed, hydrating the substrate to desired level.

The substrate is comprised of a complex starch medium, which is a source of carbon and other nutrients during the fermentation. A complex starch medium includes tuber and root crops, such as sugar beets, cassava, and potatoes, and other hard, starchy crops, such as plantains. In an exemplary embodiment, the complex starch medium is potato or potato waste. To increase the surface area of the complex starch medium and aid in oxygen transfer during the fermentation process, the complex starch medium may be ruptured with shear force. The surface area of the complex starch medium should be optimized, such as in cubes, instead of maximized because complex starch mediums with maximized surface areas have not produced as much xanthan as complex starch mediums with optimized surface areas. In the exemplary embodiment, the medium is cut into small pieces, such as into ¼ inch to ½ inch cubes, using a food processor. The size and shape of the medium and the method of achieving such size and shape are only exemplary; those skilled in the art will recognize other methods that may be used.

The substrate is provided in a fermentation vehicle of desired size. The fermentation vehicle must maintain the appropriate supply of oxygen and other chemicals to the bacteria. Baffles may be included inside the fermentation vehicle to help accomplish this. The choice of fermentation vehicle also affects the energy required for the fermentation process. For example, the use of a rotating reactor with baffles is more energy efficient.

In addition to oxygen, the fermentation process also requires nutrients for the bacteria. These nutrients may come from the complex starch medium or from supplements added to the substrate. For example, the composition of the substrate may be altered by adding nitrogen or phosphorus sources to the fermentation vehicle. In the exemplary method, 0.25 grams of $K_2HPO_4*3H_2O$ were added to about 50 grams of potato medium. Additionally, the substrate composition may be altered by adding vegetables, fruits, or their residues. Other nutrients that are known to one skilled in the art to aid in the fermentation process may be added.

Depending on the type of substrate, the substrate may be hydrated with water to achieve a desired concentration of nutrients. For semi-solid state fermentation, water is added to the substrate until the total solids content of the substrate is about 6.5% or higher; no water is added for solid state fermentation. In contrast to both the semi-solid and solid state fermentation substrates, the submerged fermentation substrate contains a large amount of water and a low concentration of nutrients. The water content of the substrate is important because it affects the amount of solvents required for the extraction process. For example, two to three volumes of alcohol are required per volume of water for precipitation in submerged fermentation. Therefore, significantly smaller quantities of solvents are used in the xanthan extraction of the presented method than in submerged fermentation because of the lower water content of the substrate.

After providing the substrate, the substrate is sterilized, as represented in Step 110 of FIG. 1. The serialization destroys microorganisms already present in the substrate. A standard sterilization procedure for a 50 gram sample is 15 minutes at 121° C. The time and temperature may vary depending on the apparatus used in the sterilization procedure. Sterilization procedures and variations thereof are known by one skilled in the art.

Next, the substrate is cooled as represented in Step 120 of FIG. 1. The substrate should be cooled to or below the maximum temperature that the inoculating bacteria can withstand. In the exemplary method, which uses *Xanthomonas campestris* bacteria that cannot withstand temperatures in excess of about 45° C.-50° C., the substrate is cooled below about 40° C. One method of cooling the substrate is to store the substrate at room temperature until the substrate obtains room temperature. Other methods to cool the substrate, which are known to one skilled in the art, may be used.

As represented in Step 130 of FIG. 1, after the substrate is cooled, the bacteria *Xanthomonas campestris* or related, genetically modified or unmodified organisms are inoculated aseptically into substrate in the fermentation vehicle. For example, *Xanthomonas campestris* NRRL B-1459, NRRL B-1003, or NRRL B-1043 may be used. In the exemplary embodiment, the *Xanthomonas campestris* inoculum is grown on the standard medium for 1 to 4 days prior to adding it to the substrate. Methods for growing bacteria as inoculum are known to one skilled in the art.

Next, as represented in Step 140 of FIG. 1, the substrate is incubated to promote the fermentation process. The incubation temperature may be between about 20-33° C., with the preferred incubation temperature being about 28° C. In the exemplary embodiment, the incubation takes place for about 72-144 hours. For the exemplary embodiment, the fermentation process does not begin to slow down until after 72 hours of incubation and does not significantly slow down until after 144 hours. Therefore, while the substrate may be incubated for less than 72 hours or more than 144 hours, these processes will not be as efficient as incubating for 72-144 hours.

Agitation may or may not accompany incubation. Agitation helps the fermentation process by increasing the transfer of oxygen and other chemicals to the substrate. In one embodiment of the method, the incubation takes place in a rotary-shaker that is maintained at 150-350 revolutions per minute (RPMs) for 72-144 hours.

In an alternative embodiment, the substrate is incubated in a rolling bottle. Agitation in a rolling bottle is maintained at a lower speed, such as 5 RPM, than a rotatory-shaker or other types of mixing devices. Additionally, the rolling bottle may also have baffles to increase the oxygen transfer to the substrate. The rolling bottles maintain the appropriate supply of oxygen and other chemical to the bacteria while consuming less energy than other apparatuses that require power intensive aerating and mixing devices. Thus, the use of rotating/rolling reactors results in a more energy efficient fermentation process. Other agitation apparatuses and methods known to one skilled in the art may be used during incubation.

Following incubation, the fermented substrate is heat treated to destroy bacteria in the fermented substrate, as represented in Step 150 of FIG. 1. One heat treatment is sterilization. Sterilization is performed using the procedure described above. Alternately, other heat treatment methods, such as pasteurization, which are known to one skilled in the art, may be used.

Following sterilization or similar heat treatment, the fermented substrate is either diluted with water or washed with water, as represented in Steps **160*a* and 160*b* of FIG. 1. Any type of clean water, such as tap or distilled, may be used for dilution or washing. Substrate is diluted or washed until the xanthan fermented is dissolved in it, as recognized by one skilled in the art. Washing can be repeated, as represented in Step 170 of FIG. 1, and wash water combined, as indicated in Step 180 of FIG. 1**.

Following dilution or water washing, the substrate is cold pressed, filtered or centrifuged to separate xanthan containing water from unused residue, as represented in Steps 190 and 210 of FIG. 1. Although FIG. 1 shows a heat treating the substrate first, the substrate may be washed or diluted first. However, it is preferred that the heat treatment is done prior to dilution or washing to lessen the amount of energy required for the process. That is, treating only the substrate requires less energy than treating a diluted mixture of the substrate and water.

Finally, as represented in Step 200 of FIG. 1, the xanthan is isolated. Isolation is accomplished by adding a salt, such as KCl, and an alcohol or acetone, such as 98% $C_2H_5OH$, as solvents to the fermented substrate. The salt is added until the salt concentration in the substrate is about 1%. The alcohol is added until the alcohol concentration in the substrate is greater than or equal to 71%. After the addition of the salt and the alcohol, gel-like xanthan precipitate from the alcohol-salt-water mixture. The xanthan may be recovered from the mixture by centrifugation, filtration or other techniques as recognized by one skilled in the art.

After the xanthan is recovered, the unused substrate may be utilized as a protein-enriched animal feed. The protein content of the unused substrate makes it suitable for use as either an animal feed or animal feed supplement. One method of disposal is to utilize the residue as a protein-enriched animal feed component. The nitrogen content of the residue makes it appealable for use in animal feed. For example, the residue may be used either as an animal feed or as an animal feed supplement.

The following examples further illustrate the present methods of solid and semi-solid state fermentation of xanthan and are not intended to limit the same.

Example 1

50 mL of standard glucose substrate of the composition listed in Table 1 and 50 grams of potato waste substrate of the composition listed in Table 1 were added into 500 mL Erlenmeyer flasks and sterilized for 15 minutes at 121° C. After cooling, 5.0 ml of *Xanthomonas campestris* NRRL B-1459 suspension, which had been grown on standard medium for 3 days, was added as inoculum. The flasks were incubated on the rotary-shaker at 28° C. and 250 RPM for 4 days. After dilution with de-ionized, distilled water ($ddH_2O$) and sterilization, raw xanthan was isolated after the addition of KCl to 1% and precipitation with 98% $C_2H_5OH$ to make the final $C_2H_5OH$ concentration >71%. The results in Table 1 show that more xanthan was produced in the solid state fermentation with a potato waste medium than was produced in the submerged fermentation with a standard glucose medium, where both fermentations were incubated at 250 RPM.

TABLE 1

| Item | Amount or Remark | |
|---|---|---|
| Medium | Standard Glucose | Potato Waste |
| Glucose | 1.00 g | 0.0 g |
| Potato Waste | 0.0 g | 49.99 g |
| Yeast extract | 0.25 g | 0.0 g |
| $K_2HPO_4 \cdot 3H_2O$ | 0.25 g | 0.25 g |
| $MgSO_4 \cdot 7H_2O$ | 0.01 g | 0.0 g |
| $H_2O$ | 50.0 mL | 0.0 mL |
| Fermentation Mode | Submerged | Solid |
| Incubated at | 250 RPM | 250 RPM |
| Xanthan after 4 days | 0.328 ± 0.007 g | 0.656 ± 0.054 g |

Example 2

By the procedures of Example 1, the set of experiments was repeated with a semi-solid state fermentation of the potato waste medium as indicated in Table 2. As shown in Table 2, the semi-solid state fermentation with a potato waste medium produced more xanthan than the submerged fermentation with a standard glucose medium, where both fermentations were incubated at 250 RPM.

TABLE 2

| Item | Amount or Remark | |
|---|---|---|
| Medium | Standard Glucose | Potato Waste |
| Glucose | 1.00 g | 0.0 g |
| Potato Waste | 0.0 g | 50.40 g |
| Yeast extract | 0.25 g | 0.0 g |
| $K_2HPO_4 \cdot 3H_2O$ | 0.25 g | 0.25 g |
| $MgSO_4 \cdot 7H_2O$ | 0.01 g | 0.0 g |
| $H_2O$ | 50.0 mL | 25.0 mL |
| Fermentation Mode | Submerged | Semi-solid |
| Incubated at | 250 RPM | 250 RPM |
| Xanthan after 4 days | 0.388 ± 0.010 g | 0.492 ± 0.007 g |

Example 3

By the procedures of Example 1, the set of experiments was repeated using *Xanthomonas campestris* NRRL B-1003 with changes indicated below and in Table 3.

50 grams of potato waste substrate of the following composition were added into 1,000 mL rolling bottles and sterilized for 15 minutes at 121° C. After cooling, 5.0 ml of *Xanthomonas campestris* NRRL B-1003 suspension, which had been grown on standard medium for 3 days, was added as inoculum. The bottles containing the potato substrate were incubated on the rolling apparatus at 28° C. and 5.0 RPM for 4 days. After dilution with $ddH_2O$ and sterilization, raw xanthan was isolated after the addition of KCl to 1% and precipitation with 98% $C_2H_5OH$ to make the final $C_2H_5OH$ concentration >71%. The results in Table 3 show that more xanthan was produced in the solid state fermentation than was produced in the submerged fermentation when both fermentations were incubated at 5.0 RPM.

TABLE 3

| Item | Amount or Remark | |
|---|---|---|
| Medium | Standard Glucose | Potato Waste |
| Glucose | 1.00 g | 0.0 g |
| Potato Waste | 0.0 g | 48.56 g |
| Yeast extract | 0.25 g | 0.0 g |
| $K_2HPO_4 \cdot 3H_2O$ | 0.25 g | 0.25 g |
| $MgSO_4 \cdot 7H_2O$ | 0.01 g | 0.0 g |
| $H_2O$ | 50.0 mL | 0.0 mL |
| Fermentation Mode | Submerged | Solid |
| Incubated at | 5.0 RPM | 5.0 RPM |
| Xanthan after 4 days | 0.207 ± 0.024 g | 0.565 ± 0.032 g |

Example 4

By the procedures of Example 1, the set of experiments was repeated using *Xanthomonas campestris* NRRL B-1003 and with a semi-solid state fermentation of the potato waste substrate. The changes are indicated in Table 4. The results in Table 4 show that more xanthan was produced in the semi-solid state fermentation than was produced in the submerged fermentation when both fermentations were incubated at 5 RPM.

TABLE 4

| Item | Amount or Remark | |
|---|---|---|
| Medium | Standard Glucose | Potato Waste |
| Glucose | 1.00 g | 0.0 g |
| Potato Waste | 0.0 g | 51.06 g |
| Yeast extract | 0.25 g | 0.0 g |
| $K_2HPO_4 \cdot 3H_2O$ | 0.25 g | 0.25 g |
| $MgSO_4 \cdot 7H_2O$ | 0.01 g | 0.0 g |
| $H_2O$ | 50.0 mL | 25.0 mL |
| Fermentation Mode | Submerged | Semi-solid |
| Incubated at | 5.0 RPM | 5.0 RPM |
| Xanthan after 4 days | 0.203 ± 0.021 g | 0.396 ± 0.002 g |

Example 5

50 mL of standard glucose substrate of the composition listed in Table 5 were added into 500 mL Erlenmeyer flasks and sterilized for 15 minutes at 121° C. After cooling, 5.0 ml of *Xanthomonas campestris* NRRL B-1459 suspension, which had been grown on standard medium for 3 days, was added as inoculum. The flasks containing the standard substrate were incubated on the rotary-shaker at 28° C. and 250 RPM for 4 days.

50 grams of potato waste substrate of the composition listed in Table 5 were added into 1,000 mL rolling bottles and sterilized for 15 minutes at 121° C. After cooling, 5.0 ml of *Xanthomonas campestris* NRRL B-1459 suspension, which had been grown on standard medium for 3 days, was added as inoculum. The bottles containing the potato medium were incubated on the rolling apparatus at 28° C. and 5.0 RPM for 4 days.

After dilution with $ddH_2O$ and sterilization, raw xanthan was isolated after the addition of KCl to 1% and precipitation with 98% $C_2H_5OH$ to make the final $C_2H_5OH$ concentration >71%. As the results in Table 5 show, more xanthan was produced using solid and semi-solid state fermentation of potato waste medium incubated at 5 RPM than was produced using submerged fermentation of a standard glucose medium incubated at 250 RPM.

TABLE 5

| Item | Amount or Remark | | |
|---|---|---|---|
| Medium | Standard Glucose | Potato Waste | Potato Waste |
| Glucose | 1.00 g | 0.0 g | 0.0 g |
| Potato Waste | 0.0 g | 50.29 g | 48.68 g |
| Yeast extract | 0.25 g | 0.0 g | 0.0 g |
| $K_2HPO_4*3H_2O$ | 0.25 g | 0.25 g | 0.25 g |
| $MgSO_4*7H_2O$ | 0.01 g | 0.0 g | 0.0 g |
| $H_2O$ | 50.0 mL | 25.0 mL | 0.0 mL |
| Fermentation Mode | Submerged 250 RPM | Semi-solid 5.0 RPM | Solid 5.0 RPM |
| Incubated at Xanthan after 4 days | 0.353 ± 0.026 g | 0.428 ± 0.034 g | 0.668 ± 0.080 g |

Example 6

50 mL of standard glucose substrate of the composition listed in Table 6 were added into 500 mL Erlenmeyer flasks and sterilized for 15 minutes at 121° C. After cooling, 5.0 ml of *Xanthomonas campestris* NRRL B-1003 suspension, which had been grown on standard medium for 3 days, was added as inoculum. The flasks containing the standard medium were incubated on the rotary-shaker at 28° C. and 250 RPM for 4 days.

50 grams of potato waste substrate of the composition listed in Table 6 were added into 1,000 mL rolling bottles and sterilized for 15 minutes at 121° C. After cooling, 5.0 ml of *Xanthomonas campestris* NRRL B-1003 suspension, which had been grown on standard medium for 3 days, was added as inoculum. The bottles containing the potato medium were incubated on the rolling apparatus at 28° C. and 5.0 RPM for 4 days.

After dilution with $ddH_2O$ and sterilization, raw xanthan was isolated after the addition of KCl to 1% and precipitation with 98% $C_2H_5OH$ to make the final $C_2H_5OH$ concentration >71%. As the results in Table 6 show, more xanthan was produced using solid and semi-solid state fermentation of potato waste medium incubated at 5 RPM than was produced using submerged fermentation of a standard glucose medium incubated at 250 RPM.

TABLE 6

| Item | Amount or Remark | | |
|---|---|---|---|
| Medium | Standard Glucose | Potato Waste | Potato Waste |
| Glucose | 1.00 g | 0.0 g | 0.0 g |
| Potato Waste | 0.0 g | 48.12 g | 51.15 g |
| Yeast extract | 0.25 g | 0.0 g | 0.0 g |
| $K_2HPO_4*3H_2O$ | 0.25 g | 0.25 g | 0.25 g |
| $MgSO_4*7H_2O$ | 0.01 g | 0.0 g | 0.0 g |
| $H_2O$ | 50.0 mL | 25.0 mL | 0.0 mL |
| Fermentation Mode | Submerged 250 RPM | Semi-solid 5.0 RPM | Solid 5.0 RPM |
| Incubated at Xanthan after 4 days | 0.333 ± 0.062 g | 0.401 ± 0.046 g | 0.630 ± 0.103 g |

As illustrated by the above examples, the presented solid and semi-solid state fermentation processes yield substantial economical and environmental benefits when compared to submerged fermentation for the production of xanthan gum. First, the solid and semi-solid fermentations produced more xanthan than the submerged fermentation, as seen in Examples 1-6. Therefore, there is an obvious economical benefit of the presented method. Second, the solid and semi-solid state fermentations contain a lower water content substrate than the submerged fermentation and, thus, require less solvents to isolate the xanthan. Therefore, economically, it is less expensive to isolate the xanthan because less solvents are required for the presented method and environmentally, there are less solvents to dispose or recycle of after isolating the xanthan. Third, when a rolling container is used as the fermentation vehicle, the appropriate amount of oxygen and other chemicals are supplied to the bacteria, as illustrated by the xanthan production, while energy requirements pertinent to the oxygen supply and mixing caused by utilization of power intensive aeration and mixing devices are minimized. This results in a more energy efficient process and economic and environmental benefits. Fourth, a complex starch medium, such as the potato waste used in the above examples, is likely to be less expensive than the glucose medium that is typically used in submerged fermentation, yielding an economic advantage. Additionally, one skilled in the art will recognize that there are other advantages of the solid and semi-solid fermentations that are not mentioned here.

From the above disclosure, producing xanthan can be achieved by providing a substrate having a total solids content of at least about 6.5% that is comprised of a complex starch medium. The complex starch medium may be root or tuber crops, such as potatoes; it may be a raw crop, a processed crop or a waste residue of the crop. For example, raw potato, processed potato or potato waste may be used as the medium. The pieces of the medium may be broken into smaller fragments using various types of grinding equipment. A nitrogen or phosphorus source or a combination of both may be added to change the nutritional composition of the substrate. For semi-solid state fermentation water is added to the substrate; no water is added for solid state fermentation. Next, the substrate is sterilized, cooled, and then inoculated with bacteria of the genus *Xanthomonas*. After inoculation, the substrate is incubated and may be agitated in a fermentation vehicle, which may be a rolling container with or without baffles. Following incubation, the fermented substrate is heat treated to destroy bacteria, diluted, and the xanthan is isolated.

Although the present invention has been described with reference to preferred embodiments, one skilled in the art will recognize that changes may be made in form and detail without departing from the spirit and scope of the invention.

What is claimed is:

1. A method for the production of xanthan by microbial conversion of a complex starch in solid form comprising the steps of:
providing a substrate comprising a complex starch medium wherein the total solids content of the substrate is at least about 6.5%;
sterilizing the substrate;
cooling the substrate;
inoculating bacteria of the genus *Xanthomonas* into the substrate, wherein the substrate is not subjected to hydrolysis prior to inoculating the bacteria of the genus *Xanthomonas*;
incubating the substrate;
heat treating the substrate;
diluting or washing the substrate to destroy the bacteria of the genus *Xanthomonas*; and
isolating xanthan.

2. The method of claim 1, wherein the complex starch medium is selected from the group consisting of root and tuber crops.

3. The method of claim 1, wherein the complex starch medium is raw or processed potato.

4. The method of claim 1, wherein the complex starch medium is potato waste.

5. The method of claim 1, further comprising: rupturing the complex starch medium with shear force to optimize surface area of the complex starch medium.

6. The method of claim 1, further comprising: adding a nitrogen source to alter the composition of the substrate.

7. The method of claim 1, further comprising: adding a phosphorus source to alter the composition of the substrate.

8. The method of claim 1, further comprising: hydrating the substrate prior to incubation, wherein the substrate after hydration has a total solids content of at least about 6.5%.

9. The method of claim 1, further comprising: agitating the substrate.

10. The method of claim 8, wherein the substrate is agitated in a rolling container.

11. The method of claim 8, wherein the substrate is agitated at a speed below about 150 revolutions per minute (RPM).

12. A method for the production of xanthan by microbial conversion, wherein the method comprises the steps of:
providing a substrate comprising a potato medium, wherein the total solids content of the substrate is at least about 6.5%;
sterilizing the substrate;
cooling the substrate;
inoculating *Xanthomonas campestris* bacteria into the substrate, wherein an external source of water is not added to the substrate prior to inoculating the *Xanthomonas campestris* bacteria;
incubating the substrate;
heat treating the substrate to destroy the bacteria of the genus *Xanthomonas*;
diluting or washing the substrate; and
isolating xanthan.

13. The method of claim 12, further comprising: adding a nitrogen source to the substrate to alter the nutritional content of the substrate.

14. The method of claim 12, further comprising: adding a phosphorus source to the substrate to alter the nutritional content of the substrate.

15. The method of claim 12, further comprising: hydrating the substrate, wherein the substrate after hydration has a total solids content of at least about 6.5%.

16. The method of claim 12, further comprising: rupturing the potato medium with shear force to optimize surface area of the potato medium.

17. The method of claim 12, wherein the *Xanthomonas campestris* bacteria is selected from the group consisting of *Xanthomonas campestris* NRRL B-1003, NRRL B-1459, and NRRL B-1043, or related bacteria either genetically modified or unmodified.

18. The method of claim 12, further comprising: agitating the substrate.

19. The method of claim 18, wherein the substrate is agitated at a speed below about 150 revolutions per minute.

* * * * *